United States Patent [19]
Christensen et al.

[11] Patent Number: 6,025,185
[45] Date of Patent: *Feb. 15, 2000

[54] FUNGUS WHEREIN THE AREA GENE HAS BEEN MODIFIED AND AN AREA GENE FROM *ASPERGILLUS ORYZAE*

[75] Inventors: Tove Christensen, Lyngby, Denmark; Michael J. Hynes, Melbourne, Australia

[73] Assignee: Novo Nordisk Als, Bagsvaerd, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,458
[22] PCT Filed: Jun. 19, 1995
[86] PCT No.: PCT/DK95/00254
　§ 371 Date: Dec. 3, 1996
　§ 102(e) Date: Dec. 3, 1996
[87] PCT Pub. No.: WO95/35385
　PCT Pub. Date: Dec. 28, 1995

[30] Foreign Application Priority Data

Jun. 17, 1994 [DK] Denmark .................... 0717/94

[51] Int. Cl.[7] ............................................. C12N 5/10
[52] U.S. Cl. ............................... 435/254.11; 435/69.1; 435/91.4; 435/172.1; 435/253.2; 435/325; 536/23.74
[58] Field of Search ............... 435/69.1, 253.2, 435/325, 254.11, 172.1, 91.4; 536/23.74

[56] References Cited

U.S. PATENT DOCUMENTS 5,179,003　1/1993　Wolf et al. .................... 435/69.1
5,190,931　3/1993　Inouye .......................... 435/240.2

FOREIGN PATENT DOCUMENTS 0184438　6/1986　European Pat. Off. .
0206783　12/1986　European Pat. Off. .
0238023　9/1987　European Pat. Off. .
WO 90/00192　1/1990　WIPO .
WO 92/17595　10/1992　WIPO .

OTHER PUBLICATIONS

Molec. gen. Genet. vol. 126, pp. 111–141 (1973).
The EMBO Journal, vol. 5, pp. 1087–1090 (1986).
Molecular Microbiology vol. 7(1), pp. 81–87 (1993).
Books of Abstracts, 2nd European Conference on Jungal Genetics Apr. 28–May 1, 1994 1 page.
Bio\Technology, vol. 5, pp. 1301–1304 (1987).
Gene, vol. 95, pp. 123–127 (1990).
The EMBO Journal, vol. 9, No. 5, pp. 1355–1364 (1990).
Upshall et al. (1987) Bio/technology 5:1301–134.
Stankovitch et al. (1993) 7:81–87 Molec Microbiol.
Y.H. Fu et al., Molecular Microbiology, (1990), 4 (11), pp. 1847–1852.
Xiao Dong Xiao et al., Current Genetics (1993) 24: pp. 212–218.
Ying–Hui Fu, Molecular And Cellular Biology, Mar. 1990, pp. 1056–1065.
B.L. Cohen, Trans. Br. Mycol. Soc. 76 (3) pp. 447–450 (1981).
B.L. Cohen, Journal of General Microbiology (1972), 71, pp. 293–299.
B.L. Cohen, Journal of General Microbiology (1973), 79, pp. 311–320.
Tove Christensen et al., Applied And Environmental Microbiology, Sep. 1998, pp. 3232–3237.

*Primary Examiner*—Elizabeth Kemmerer
*Assistant Examiner*—David S. Romeo
*Attorney, Agent, or Firm*—Steve T. Zelson; Valeta Gregg

[57] ABSTRACT

A modified *Aspergillus oryzae* cell having an area gene which does not express a functional AreA activator, DNA sequences encoding the area gene, and method for using the cell of the invention for production of a heterologous polypeptide.

8 Claims, 6 Drawing Sheets

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 5643 base pairs
      (B) TYPE: nucleic acid (C) STRANDEDNESS: single
          (D) TOPOLOGY: linear (vi) ORIGINAL SOURCE:
         (A) ORGANISM: Aspergillus oryzae
         (B) STRAIN: IFO4177

(ix) FEATURE:
         (A) NAME/KEY: intron
         (B) LOCATION: 2701..2769

(ix) FEATURE:
         (A) NAME/KEY: CDS
         (B) LOCATION: join(2282..2700, 2770..4949)

(xi) SEQUENCE DESCRIPTION: SEQ ID NO: 1:

```
AAGCTTCGTC CTCGCATCTC GGCCGGGTGA GTAAGGTATG GTATTATTCA TGAAGGGATC      60

TCGTTGGTTA CCGTTGTCTA TCCCTAAACA AAGGATTCAA GAGAACAACT CGGAATGCTC     120

CCTCCGCTTA AACCCCTTGA CTCACTGATG GTGTATGTAC TATGGGTACG ACGTTCGGGA     180

TGTGGACTAC CAACCAGAGA GTGATTAGAG AGTCCGGGTT CTCAGTCCAT GATTTTTGCA     240

TCTTTGAAAC AGACGATGCG GAGCGGTCAT TGGCGGAGTT TACTCCCAAA TACGGCCGAA     300

CGGGGTACTT TAAGTGGAAT CTCCGATTTT GGATCTAAGC TCATGAAGGA AAAGTACTAC     360

TAATGCGTAC CTGTGCCTAA TGTTAGTGCT AGTTCGTCTG TTGCATTTTA CCCGTCGGTT     420

AAGACGAATG GATCCGTTCA GGTTTTAAAA TAACTATCTA TGAAATATTT TAGATTTCCC     480

GACATAGTGG TTGGGATGTC TCGATTAACA CTAGGTACAT CAGGCTCAAT TGATTTTGGT     540

TTTAACGAAA CATGATATAG GTCAGGGTCG TGGACCACCC TCCGCCAGGG ATCAGGGGAC     600

GGTTACATGC GAAGGATTCT GATTATATTC ATGATTATGT CAAGCCTTTT CTCTCGTGTG     660

AAGAGGAGCA GAGAATCCGT ACGGGTTTAA TTTAATTTAG CGCCCTGCAG CTTCGAGAAC     720

ATCCCCAGCA ACGTTAAAAA CCACGAGCTA AAATGGGTCG CCACCGGAAG CACTCGAGTC     780

GAGAGATCGG TCGGCTCAGT ATTCGTAATA CCTGCGTTCC AGACGGTTTT GGTCGTTGGT     840

TTCACTCAGG GAACTTAATT CCAGCGGGAC CCAATATAAT TTGAATGATT CATGATACAT     900

CCATTCGTTT GAACCGATCC TGCAAGAGTT CTGTCTGATT TGGTCAACAT AGTTTTCCTC     960

TGGGGGAGAC TGGGGAAGAG TCAACACAAT GGTCAGGGAG AGAAGAATGA AAGCTCTCGC    1020

AAGTGGATGA TCATGCTACG TACTGTAGGA ATAAAATTAA TTAATGCGAG GCTGCAAGTA    1080

TCCCTGCGCC GATTTCTCT TCTTACGGCG GGAACCAAAA AATGTGACGC TGTGATTTTC     1140

TGGAAAAGGT AAGGATGTTT AGTTTCCCAG GATTATTACT GGTTCCGTAT GTGTATGTGT    1200

ATGGATATCA TTCCGTATGG ATACGCCCGT TTCCTCCGCC CAGAACCAGT CCGTCATCCA    1260

TCCTCCACTC TTTCTTCTCT TAGAGCCTTT CCACCTCTCT TCACTTTCTT TTTCTTTCCC    1320

CCCTCCCTCT TTGCTTTCCC TCTCCCAGTA TTATTCTTAT ATTATCGGTT TGACCGTCGC    1380

CTCAGTATCG GCCCCCCGTG AATCACTTTT CGTTTCTCTT GTATTTTACT TTCCTATCTG    1440

GGATTGCTCC TCGATTAGCA GCTCTACTTC ATTCGGCCAT GTGCGTCTAG AGGGTCTAGC    1500

CCCTCTCTCT CTTTGCACTG ACTGTCAGCC ATACCATAGT ATCATCCCGG AATTAAGAAA    1560

AAAAAGAAA TTATTCTACC TCCGATCTGG ACAAATTATA ACCAGGAGAA AATCAAGCGA     1620

AAGAGGGGCA AAGGAGGAGA CACCATTAAA ACTGGGTCTG GTTTGATTCA TGACATACAT    1680

TCGTCGTCTT GAATTTCAAT AGGTACGGAC TGATGCATTC CACTCGAGCC TTTTTAGCTG    1740

CGTGTCCGTC TCCAATCGCA CTTCTTTTCT TATTTCCTTG TGGGATAAAT TGATTATTTA    1800

CCGTTTCGTT TTCTCTATAT TGCGGTGGTG GTGCGACCCA TCCAACTATT ATTATTATAA    1860
```

```
TTGGAATTTG ATTTGGATTT TGATTCCTGT GACGGATCTC AGACCAAGTG CCTAAACTAT    1920

AACTGACTTG GACCCCCTTC AGATCCTAGC TTCCCGATTC TTTTCCACCA CTGCTGCATC    1980

CTCTTCCTGC ACGCAGCGTT CGTTTAGGGC GGGTAGACTG GAATTTATTC CTTGCGCCAC    2040

GGACCAATCG CTCCCTCGAC GCTCTCATTC CTGCGTCGAG CTCTTTTTCC CTCGACTCTC    2100

ATTGCTTGCT GGGCTGGTTC TTGAACCTCT TCAATCGTCC TTATCTCTTT CCCCCCATCC    2160

GGCCTGTGAT TCCTATCTTT CCTTTTTTTC TTCCCTTTCT TGTTTGATCC CCCCTCCTCC    2220

CCGTCTTATC GCCTACTATC GTGATCCCCG CCCTTCCCAA TAAAGAGTAG GGCGTGTGAA    2280

C ATG TCC GGG TTA ACC CTC GGG CGA GGC CCT GGG GGC GTG CGA CCG         2326
  Met Ser Gly Leu Thr Leu Gly Arg Gly Pro Gly Gly Val Arg Pro
  1               5                  10                  15

ACT CAA ACC GCA ACT TTT ACC ACC CAC CAC CCG TCC GCC GAT GCT GAC       2374
Thr Gln Thr Ala Thr Phe Thr Thr His His Pro Ser Ala Asp Ala Asp
                    20                  25                  30

CGC TCC TCC AAC AAC CTC CCC CCT ACC TCC TCG CAG CTG TCC GAT GAC       2422
Arg Ser Ser Asn Asn Leu Pro Pro Thr Ser Ser Gln Leu Ser Asp Asp
                35                  40                  45

TTT TCT TTC GGT TCC CCT CTG AGC CCC GCC GAC TCA CAG GCC CAT GAC       2470
Phe Ser Phe Gly Ser Pro Leu Ser Pro Ala Asp Ser Gln Ala His Asp
            50                  55                  60

GGC CTA CTT CAG GAC TCC CTC TTC CCT GAA TGG GGG TCT GGT GCG CCT       2518
Gly Leu Leu Gln Asp Ser Leu Phe Pro Glu Trp Gly Ser Gly Ala Pro
        65                  70                  75

CGA CCC GGC ATT GAC AGT CCG GAT GAG ATG CAG AGG CAA GAT CCG CTA       2566
Arg Pro Gly Ile Asp Ser Pro Asp Glu Met Gln Arg Gln Asp Pro Leu
    80                  85                  90                  95

GCG ACT CAA ATA TGG AAG CTC TAT TCT AGG ACC AAG GCC CAG TTG CCC       2614
Ala Thr Gln Ile Trp Lys Leu Tyr Ser Arg Thr Lys Ala Gln Leu Pro
                    100                 105                 110

AAC CAG GAG CGT ATG GAA AAC CTG ACC TGG CGG ATG ATG GCG ATG AGT       2662
Asn Gln Glu Arg Met Glu Asn Leu Thr Trp Arg Met Met Ala Met Ser
                115                 120                 125

TTG AAA CGT AAG GAG CGG GAA CGT GCT CAA CAG TCC    AT GTAGGTGTTC      2710
Leu Lys Arg Lys Glu Arg Glu Arg Ala Gln Gln Ser    Met
            130                 135                 140

TCCCTCTGTA GAGGAACGGC TGGACCCGCT CATCATTAAT TTTTTTTTTG TCTGTGAAG G    2770

TTT CCT GCG AGA CGC GGT AGC GCT GGC CCC AGT GGT ATC GCT CAA CTG       2818
Phe Pro Ala Arg Arg Gly Ser Ala Gly Pro Ser Gly Ile Ala Gln Leu
                    145                 150                 155

CGC ATT TCC GAC CCG CCC GTT GCC ACC GGT AAC CCT CAG TCA ACC GAC       2866
Arg Ile Ser Asp Pro Pro Val Ala Thr Gly Asn Pro Gln Ser Thr Asp
                160                 165                 170

CTG ACC GCC GAC CCT ATG AAC CTC GAC GAT TTC ATC GTG CCC TTC GAA       2914
Leu Thr Ala Asp Pro Met Asn Leu Asp Asp Phe Ile Val Pro Phe Glu
            175                 180                 185

TCT CCT TCG GAC CAC CCC TCG CCC AGT GCC GTC AAG ATT TCC GAC TCC       2962
Ser Pro Ser Asp His Pro Ser Pro Ser Ala Val Lys Ile Ser Asp Ser
        190                 195                 200

ACG GCG TCC GCG GCC ATT CCC ATC AAG TCC CGG AAA GAC CAG CTG AGA       3010
Thr Ala Ser Ala Ala Ile Pro Ile Lys Ser Arg Lys Asp Gln Leu Arg
205                 210                 215                 220

GAT TCT ACC CCG GTG CCG GCC TCG TTC CAC CAT CCG GCT CAG GAT CAA       3058
Asp Ser Thr Pro Val Pro Ala Ser Phe His His Pro Ala Gln Asp Gln
                225                 230                 235

CGG AAG AAC AGT GAA TTT GGC TAC GTC CCC CGT CGC GTG CGC AAG ACG       3106
Arg Lys Asn Ser Glu Phe Gly Tyr Val Pro Arg Arg Val Arg Lys Thr
                240                 245                 250
```

```
AGT ATC GAC GAG CGT CAA TTT TTC TCA CTG CAG GTG CCG ACC CGA AAG      3154
Ser Ile Asp Glu Arg Gln Phe Phe Ser Leu Gln Val Pro Thr Arg Lys
        255                 260                 265

CGA CCG GCC GAA TCC TCG CCC CAG GTA CCC CCC GTT TCC AAC TCG ATG      3202
Arg Pro Ala Glu Ser Ser Pro Gln Val Pro Pro Val Ser Asn Ser Met
    270                 275                 280

TTG GCC CAC GAT CCG GAC CTC GCT TCC GGC GTG CCC GAT TAT GCC TTG      3250
Leu Ala His Asp Pro Asp Leu Ala Ser Gly Val Pro Asp Tyr Ala Leu
285                 290                 295                 300

GAC GCC CCG TCC TCG GCC TTT GGC TTC CAT CAG GGT AAC CAC CAT CCG      3298
Asp Ala Pro Ser Ser Ala Phe Gly Phe His Gln Gly Asn His His Pro
                305                 310                 315

GTC AAT CAT CAC AAC CAC ACC TCC CCC GGG GCA CCG TTT GGC TTG GAT      3346
Val Asn His His Asn His Thr Ser Pro Gly Ala Pro Phe Gly Leu Asp
            320                 325                 330

ACG TTC GGC CTG GGA GAT GAT CCA ATC TTG CCC TCC GCG GGC CCC TAC      3394
Thr Phe Gly Leu Gly Asp Asp Pro Ile Leu Pro Ser Ala Gly Pro Tyr
                335                 340                 345

CAG TCG CAA TTC ACC TTC TCA CCC AGC GAG TCT CCG ATG GCC TCC GGT      3442
Gln Ser Gln Phe Thr Phe Ser Pro Ser Glu Ser Pro Met Ala Ser Gly
        350                 355                 360

CAT CCG TTT GCG AAC CTC TAT TCG CAT ACC CCG GTG GCT TCG TCC CTC      3490
His Pro Phe Ala Asn Leu Tyr Ser His Thr Pro Val Ala Ser Ser Leu
365                 370                 375                 380

AAC TCG ACG GAT TTC TTC TCT CCA CCG CCA TCA GGC TAC CAG TCC ACG      3538
Asn Ser Thr Asp Phe Phe Ser Pro Pro Pro Ser Gly Tyr Gln Ser Thr
                385                 390                 395

GCA TCC ACG CCG CAG CCC ACC TAC GAC GGG GAC CAT TCC GTT TAT TTC      3586
Ala Ser Thr Pro Gln Pro Thr Tyr Asp Gly Asp His Ser Val Tyr Phe
            400                 405                 410

GAT ATG CCG TCG GGC GAC GCG CGC ACC CAG CGC CGC ATT CCG AAC TAT      3634
Asp Met Pro Ser Gly Asp Ala Arg Thr Gln Arg Arg Ile Pro Asn Tyr
                415                 420                 425

ATT TCG CAT CGG TCC AAC TTG TCT GCT TCG CTG CAG CCT CGG TAT ATG      3682
Ile Ser His Arg Ser Asn Leu Ser Ala Ser Leu Gln Pro Arg Tyr Met
        430                 435                 440

TTC AAC CAG AAC AAC CAT GAA CAG GCC AGT TCG TCG ACG GTG CAT TCG      3730
Phe Asn Gln Asn Asn His Glu Gln Ala Ser Ser Ser Thr Val His Ser
445                 450                 455                 460

CCG AGC TAC CCC ATT CCC CAG CCG CAA CAT GTG GAC CCC ACT CAG GTG      3778
Pro Ser Tyr Pro Ile Pro Gln Pro Gln His Val Asp Pro Thr Gln Val
                465                 470                 475

TTG AAC GCC ACC AAT TAC TCG ACC GGC AAC TCC CAC CAT ACC GGC GCC      3826
Leu Asn Ala Thr Asn Tyr Ser Thr Gly Asn Ser His His Thr Gly Ala
            480                 485                 490

ATG TTT TCA TTT GGA GCC GAT TCA GAT AAC GAG GAT GAC GAT GGT CAT      3874
Met Phe Ser Phe Gly Ala Asp Ser Asp Asn Glu Asp Asp Asp Gly His
                495                 500                 505

CAG CTG TCC GAG CGG GCT GGT CTG GCG ATG CCG ACT GAA TAT GGG GAC      3922
Gln Leu Ser Glu Arg Ala Gly Leu Ala Met Pro Thr Glu Tyr Gly Asp
        510                 515                 520

GAG GAC GGG TTC TCG TCG GGC ATG CAG TGG GAT GGG CAG TTC CCG GGC      3970
Glu Asp Gly Phe Ser Ser Gly Met Gln Trp Asp Gly Gln Phe Pro Gly
525                 530                 535                 540

TCC TTC CAT TCG CTG CCG GGC TTT GGC CCT CAA CAT CGC AAG CAT GTT      4018
Ser Phe His Ser Leu Pro Gly Phe Gly Pro Gln His Arg Lys His Val
                545                 550                 555

ACC ATC GGG TCC ACG GAC ATG ATG GAC ACC CCC GAG GAG TGG AAT CAC      4066
Thr Ile Gly Ser Thr Asp Met Met Asp Thr Pro Glu Glu Trp Asn His
```

-continued

```
           560                    565                    570
GGT GGC AGT TTG GGT CGG ACT CAT GGG TCG GTG GCT TCG GTC AGT GAG    4114
Gly Gly Ser Leu Gly Arg Thr His Gly Ser Val Ala Ser Val Ser Glu
            575                    580                585

GTG CGC AAC CGA GAG CAG GAC CCT CGC CGG CAG AAG ATT GCC CGC ACC    4162
Val Arg Asn Arg Glu Gln Asp Pro Arg Arg Gln Lys Ile Ala Arg Thr
        590                    595                600

ACG TCC ACC CCC AAT ACG GCC CAG CTG TTG CGC CAA AGC ATG CAC TCT    4210
Thr Ser Thr Pro Asn Thr Ala Gln Leu Leu Arg Gln Ser Met His Ser
605                    610                615                620

AAT AAC AAT ACG TCT CAT ACC TCC CCT AAT ACG CCG CCC GAG TCC GCC    4258
Asn Asn Asn Thr Ser His Thr Ser Pro Asn Thr Pro Pro Glu Ser Ala
                625                    630                635

CTG AGC AGC GCA GTT CCG TCC CGC CCG GCC AGT CCC GGG GGC AGC AAG    4306
Leu Ser Ser Ala Val Pro Ser Arg Pro Ala Ser Pro Gly Gly Ser Lys
            640                    645                650

AAC GGC GAC CAA GGC AGC AAC GGA CCG ACC ACC TGC ACG AAC TGC TTC    4354
Asn Gly Asp Gln Gly Ser Asn Gly Pro Thr Thr Cys Thr Asn Cys Phe
        655                    660                665

ACT CAA ACC ACT CCG CTG TGG CGT CGG AAC CCA GAG GGC CAG CCA CTG    4402
Thr Gln Thr Thr Pro Leu Trp Arg Arg Asn Pro Glu Gly Gln Pro Leu
670                    675                680

TGC AAT GCC TGC GGG TTG TTT TTG AAA TTG CAC GGT GTC GTG CGC CCT    4450
Cys Asn Ala Cys Gly Leu Phe Leu Lys Leu His Gly Val Val Arg Pro
685                    690                695                700

CTG TCC CTG AAA ACG GAC GTT ATC AAA AAG CGC AAC CGT AGC AGT GCC    4498
Leu Ser Leu Lys Thr Asp Val Ile Lys Lys Arg Asn Arg Ser Ser Ala
                705                    710                715

AAC AGC TTG GCG GTT GGG ACC TCC CGT GCG TCG AAG AAG ACA GCC CGC    4546
Asn Ser Leu Ala Val Gly Thr Ser Arg Ala Ser Lys Lys Thr Ala Arg
            720                    725                730

AAG AAC TCG GTG CAG CAA GCA TCC GTC ACG ACT CCG ACA TCA AGC CGC    4594
Lys Asn Ser Val Gln Gln Ala Ser Val Thr Thr Pro Thr Ser Ser Arg
        735                    740                745

GCT CAG AAT GGG ACT TCC TTC GAA TCC CCG CCC GCC GGC TTT AGT GCT    4642
Ala Gln Asn Gly Thr Ser Phe Glu Ser Pro Pro Ala Gly Phe Ser Ala
    750                    755                760

GCC GCG GGA CGG TCG AAT GGG GTG GTA CCC ATT GCC GCC GCT CCT CCG    4690
Ala Ala Gly Arg Ser Asn Gly Val Val Pro Ile Ala Ala Ala Pro Pro
765                    770                775                780

AAG GCA GCT CCC TCC GCA GCC GCC TCC CCT AGC ACG GGC CAG ACC CGC    4738
Lys Ala Ala Pro Ser Ala Ala Ala Ser Pro Ser Thr Gly Gln Thr Arg
                785                    790                795

AAC CCG ATC CAG GCT GCC CCG AAA CGT CAA CGA CGG CTG GAA AAG GCC    4786
Asn Pro Ile Gln Ala Ala Pro Lys Arg Gln Arg Arg Leu Glu Lys Ala
            800                    805                810

ACG GAG ATG GAA ACG GAC GAG GCT AAC AAG TCC GCG GGA GGC CGA TCC    4834
Thr Glu Met Glu Thr Asp Glu Ala Asn Lys Ser Ala Gly Gly Arg Ser
        815                    820                825

AAG GTG GTG CCT CTG GCA CCC GCC ATG CCA CCG GCA GCA GCC AAT CCG    4882
Lys Val Val Pro Leu Ala Pro Ala Met Pro Pro Ala Ala Ala Asn Pro
    830                    835                840

GCG AAC CAT AGT ATT GCC GGA GGC CAA GGG GCT AGT CAG GAA TGG GAG    4930
Ala Asn His Ser Ile Ala Gly Gly Gln Gly Ala Ser Gln Glu Trp Glu
845                    850                855                860

TGG TTG ACG ATG AGT CTGTAATGGC CGCGCTTACC TCTCTACTTC TCTACACTCG    4985
Trp Leu Thr Met Ser Leu
                865

TTTCTTAATA TCTTTCTTGA ACCCCCCCTT ATATTTTCCC ACCGTTGATG CTACGCCATG   5045
```

-continued

```
ACCGATAGAG ATGATGAATA CTGCAACCAA TGGAATCTCG CTAGACGAGA GGTGTTAGAT    5105

GACGTGGCCC GCGATGCACT TAATGAGATA CGAGGAGGTG CAATGCGTTG GTTACGCTAG    5165

TTTAATGGTA ACATGACGAG GGATATTCGC TCTGTTATTT CGGGCTTTGA TCTGTTTCAG    5225

TCTGCGATTT AACAGCGACT GATCCTCTGC TGTGACAATA CACAGCTTGT CTTGTGGTTC    5285

TGTTGTGGCT TTCTGTTTGT TTGGCTGATT TGATTTATGC TTGATACAAT CGCGTCTGTC    5345

CGGACCCCGG CCTTTGTTTT GTTTTCAGTT CTGATTCTTC ACTGTTTCTG ATTCTCTTGT    5405

TCATGTTTTT GATTTGTTCA AGGCTTGGGG CCGGGCAGAA GTGCGCATCT CTGCTTTGTG    5465

TTTTCCGTCA CCGTGCATAG ACGCTGTATG TATATGCTAC AGCAAGATTC TACTTATCCA    5525

GTCTGAGCCT GTATTCATTG AAGTGTAGCC AGCTGTCGAA TGAGCTTTTT AACGATATTG    5585

TTTTGTTGAG TAGTCAACAA GTAGTATCTG TATATTCCGG AGTCTAAGTA AGACACTT     5643
```

(2) INFORMATION FOR SEQ ID NO: 2:

(i) SEQUENCE CHARACTERISTICS:
        (A) LENGTH: 866 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Gly Leu Thr Leu Gly Arg Gly Pro Gly Gly Val Arg Pro Thr
 1               5                  10                  15

Gln Thr Ala Thr Phe Thr Thr His His Pro Ser Ala Asp Ala Asp Arg
                20                  25                  30

Ser Ser Asn Asn Leu Pro Pro Thr Ser Ser Gln Leu Ser Asp Asp Phe
            35                  40                  45

Ser Phe Gly Ser Pro Leu Ser Pro Ala Asp Ser Gln Ala His Asp Gly
        50                  55                  60

Leu Leu Gln Asp Ser Leu Phe Pro Glu Trp Gly Ser Gly Ala Pro Arg
65                  70                  75                  80

Pro Gly Ile Asp Ser Pro Asp Glu Met Gln Arg Gln Asp Pro Leu Ala
                85                  90                  95

Thr Gln Ile Trp Lys Leu Tyr Ser Arg Thr Lys Ala Gln Leu Pro Asn
               100                 105                 110

Gln Glu Arg Met Glu Asn Leu Thr Trp Arg Met Met Ala Met Ser Leu
           115                 120                 125

Lys Arg Lys Glu Arg Glu Arg Ala Gln Gln Ser Met Phe Pro Ala Arg
130                 135                 140

Arg Gly Ser Ala Gly Pro Ser Gly Ile Ala Gln Leu Arg Ile Ser Asp
145                 150                 155                 160

Pro Pro Val Ala Thr Gly Asn Pro Gln Ser Thr Asp Leu Thr Ala Asp
                165                 170                 175

Pro Met Asn Leu Asp Asp Phe Ile Val Pro Phe Glu Ser Pro Ser Asp
            180                 185                 190

His Pro Ser Pro Ser Ala Val Lys Ile Ser Asp Ser Thr Ala Ser Ala
        195                 200                 205

Ala Ile Pro Ile Lys Ser Arg Lys Asp Gln Leu Arg Asp Ser Thr Pro
    210                 215                 220

Val Pro Ala Ser Phe His His Pro Ala Gln Asp Gln Arg Lys Asn Ser
225                 230                 235                 240

Glu Phe Gly Tyr Val Pro Arg Arg Val Arg Lys Thr Ser Ile Asp Glu
```

-continued

```
                    245                 250                 255
Arg Gln Phe Phe Ser Leu Gln Val Pro Thr Arg Lys Arg Pro Ala Glu
                260                 265                 270

Ser Ser Pro Gln Val Pro Pro Val Ser Asn Ser Met Leu Ala His Asp
            275                 280                 285

Pro Asp Leu Ala Ser Gly Val Pro Asp Tyr Ala Leu Asp Ala Pro Ser
        290                 295                 300

Ser Ala Phe Gly Phe His Gln Gly Asn His His Pro Val Asn His His
305                 310                 315                 320

Asn His Thr Ser Pro Gly Ala Pro Phe Gly Leu Asp Thr Phe Gly Leu
                325                 330                 335

Gly Asp Asp Pro Ile Leu Pro Ser Ala Gly Pro Tyr Gln Ser Gln Phe
                340                 345                 350

Thr Phe Ser Pro Ser Glu Ser Pro Met Ala Ser Gly His Pro Phe Ala
            355                 360                 365

Asn Leu Tyr Ser His Thr Pro Val Ala Ser Ser Leu Asn Ser Thr Asp
        370                 375                 380

Phe Phe Ser Pro Pro Ser Gly Tyr Gln Ser Thr Ala Ser Thr Pro
385                 390                 395                 400

Gln Pro Thr Tyr Asp Gly Asp His Ser Val Tyr Phe Asp Met Pro Ser
                405                 410                 415

Gly Asp Ala Arg Thr Gln Arg Arg Ile Pro Asn Tyr Ile Ser His Arg
                420                 425                 430

Ser Asn Leu Ser Ala Ser Leu Gln Pro Arg Tyr Met Phe Asn Gln Asn
            435                 440                 445

Asn His Glu Gln Ala Ser Ser Thr Val His Ser Pro Ser Tyr Pro
        450                 455                 460

Ile Pro Gln Pro Gln His Val Asp Pro Thr Gln Val Leu Asn Ala Thr
465                 470                 475                 480

Asn Tyr Ser Thr Gly Asn Ser His His Thr Gly Ala Met Phe Ser Phe
                485                 490                 495

Gly Ala Asp Ser Asp Asn Glu Asp Asp Gly His Gln Leu Ser Glu
            500                 505                 510

Arg Ala Gly Leu Ala Met Pro Thr Glu Tyr Gly Asp Glu Asp Gly Phe
        515                 520                 525

Ser Ser Gly Met Gln Trp Asp Gly Gln Phe Pro Gly Ser Phe His Ser
530                 535                 540

Leu Pro Gly Phe Gly Pro Gln His Arg Lys His Val Thr Ile Gly Ser
545                 550                 555                 560

Thr Asp Met Met Asp Thr Pro Glu Glu Trp Asn His Gly Gly Ser Leu
                565                 570                 575

Gly Arg Thr His Gly Ser Val Ala Ser Val Ser Glu Val Arg Asn Arg
            580                 585                 590

Glu Gln Asp Pro Arg Arg Gln Lys Ile Ala Arg Thr Thr Ser Thr Pro
        595                 600                 605

Asn Thr Ala Gln Leu Leu Arg Gln Ser Met His Ser Asn Asn Asn Thr
    610                 615                 620

Ser His Thr Ser Pro Asn Thr Pro Glu Ser Ala Leu Ser Ser Ala
625                 630                 635                 640

Val Pro Ser Arg Pro Ala Ser Pro Gly Gly Ser Lys Asn Gly Asp Gln
                645                 650                 655

Gly Ser Asn Gly Pro Thr Thr Cys Thr Asn Cys Phe Thr Gln Thr Thr
                660                 665                 670
```

-continued

```
Pro Leu Trp Arg Arg Asn Pro Glu Gly Gln Pro Leu Cys Asn Ala Cys
        675             680              685
Gly Leu Phe Leu Lys Leu His Gly Val Val Arg Pro Leu Ser Leu Lys
        690             695              700
Thr Asp Val Ile Lys Lys Arg Asn Arg Ser Ser Ala Asn Ser Leu Ala
705             710             715                         720
Val Gly Thr Ser Arg Ala Ser Lys Lys Thr Ala Arg Lys Asn Ser Val
                725             730              735
Gln Gln Ala Ser Val Thr Thr Pro Thr Ser Ser Arg Ala Gln Asn Gly
                740             745              750
Thr Ser Phe Glu Ser Pro Pro Ala Gly Phe Ser Ala Ala Ala Gly Arg
        755             760              765
Ser Asn Gly Val Val Pro Ile Ala Ala Ala Pro Pro Lys Ala Ala Pro
        770             775              780
Ser Ala Ala Ala Ser Pro Ser Thr Gly Gln Thr Arg Asn Pro Ile Gln
785             790             795                         800
Ala Ala Pro Lys Arg Gln Arg Arg Leu Glu Lys Ala Thr Glu Met Glu
                805             810              815
Thr Asp Glu Ala Asn Lys Ser Ala Gly Gly Arg Ser Lys Val Val Pro
                820             825              830
Leu Ala Pro Ala Met Pro Pro Ala Ala Ala Asn Pro Ala Asn His Ser
        835             840              845
Ile Ala Gly Gly Gln Gly Ala Ser Gln Glu Trp Glu Trp Leu Thr Met
        850             855              860
Ser Leu
865
```

FUNGUS WHEREIN THE AREA GENE HAS BEEN MODIFIED AND AN AREA GENE FROM *ASPERGILLUS ORYZAE*

CROSS-REFERENCE TO RELATED APPLICATIONS

This application is a 35 U.S.C. 371 national application of PCT/DK95/00254 filed Jun. 19, 1995, which is incorporated herein by reference.

FIELD OF THE INVENTION

The present invention relates to fungi, which do not produce proteases. The fungi of the invention are useful as hosts for the production of proteins susceptible to proteolytic degradation by the proteases usually produced, and the invention consequently encompasses processes for the production of proteins of interest in high yields by using the fungi of the invention. The invention also comprises methods for producing such fungi and DNA constructs to be used in these methods.

BACKGROUND OF THE INVENTION

Fungi, and especially filamentous fungi, are widely used commercially because of their ability to secrete remarkably high levels of proteins Among the filamentous fungi species belonging to the genus Aspergillus have a long history of commercial use for the production of endogenous and lately also heterologous proteins.

One disadvantage with most microorganisms used for the production of proteins is the inherent production of proteases which may subject a protein product of interest to degradation due to proteolysis.

Various ways of avoiding this have been envisaged. Among other solutions it has been suggested to delete or disrupt the genes encoding the various proteases. Unfortunately the fungi produce a high number of proteases making such a solution more or less unrealistic.

A need is therefore persisting for strains of filamentous fungi exhibiting no or very low levels of protease production.

For a number of years it has been known that the regulatory gene areA which mediates nitrogen metabolite repression in *A. nidulans* influences the production of extracellular proteases (Arst & Cove, molec. gen. *Genet.* 126, (1973) 111–141).

The areA gene from *A. nidulans* has been cloned (Caddick et al., *EMBO Journal* 5, (1986) 1087–1090) and various modifications made to it to evaluate functions of different regions in the activator protein encoded by this gene (Stankovitch et al. *Mol. Microbiol.* 7, (1993) 81–87). Furthermore the gene coding the corresponding function in *A. fumigatus* apparently has been cloned recently (Hensel et al. 2nd European Conference on Fungal Genetics, Apr. 28 to May 1, 1994, Book of Abstracts, E11).

From the literature a single use is also known of a strain of *A. nidulans* of genotype argB areA1 as a host for the production of t-PA (Upshall et al. *Biotechnology* 5, (1987) 1301–1304). In this example only the argB genotype is used as a selection marker through its arginine prototrophy, while the area genotype is simply a coincidence.

The present invention has as an object the alleviation of the need for protease free filamentous fungi.

SUMMARY OF THE INVENTION

The present invention consequently relates to fungi, wherein the areA gene by recombinant DNA technology has been modified such that it cannot be expressed in a way providing for a functional AreA activator.

The invention furthermore relates to methods for producing such fungi, obtained by deletion of the areA gene.

This may be obtained through a method comprising
i) cloning of the areA gene from a fungus of interest,
ii) producing a DNA construct comprising the areA gene wherein an internal part has been substituted, deleted, or extra DNA has been inserted,
iii) transforming said fungus with the construct, and
iv) selecting transformants which are areA.

The information obtained from the above mentioned cloning of the areA gene may also be used in connection with the well-known anti-sense technology, to construct an expression plasmid giving rise to synthesis of a RNA molecule complementary to the mRNA transcribed from the areA gene, and to transform the fungus of interest therewith.

The invention furthermore relates to DNA constructs intended for use in the above mentioned methods.

Furthermore the invention relates to methods of producing a desired protein or gene product, especially secreted proteins, whereby a fungal host modified and optionally transformed with a DNA construct comprising at least a DNA sequence coding for the protein or gene product of interest, is cultivated in a suitable growth medium at appropriate conditions and the desired gene product is recovered and purified.

When working with the invention it was surprisingly found that the fungi of the invention produces such secreted proteins in a much improved yield.

It was also surprisingly found that the only nitrogen source capable of providing good growth of the *A. oryzae* areA strains was glutamine.

Lastly the invention relates to protein products produced by the above methods.

BRIEF DESCRIPTION OF THE DRAWING

The invention is described in further detail in the following parts of the specification with reference to the Examples and the drawing, wherein.

DEFINITIONS

Figure 1:
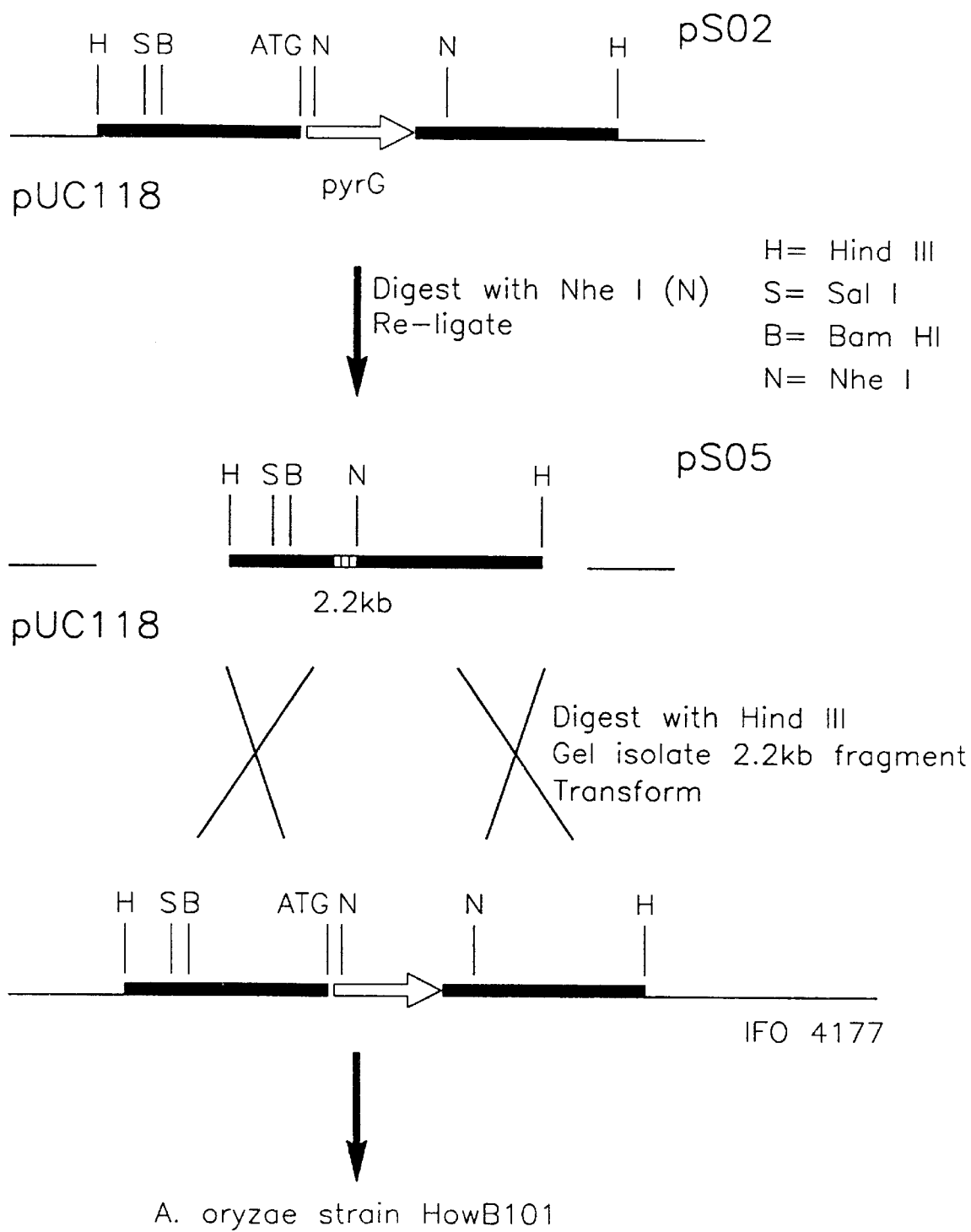
FIG. 1 shows the steps involved in the construction of HowB101.

In the present specification the following definitions are used

The expression areAΔ means a strain in which the areA gene is deleted.

The expression areA means a strain which does not produce a functional AreA activator. The term "loss of function" is also often used for this.

The expression "anti-sense technology" describes methods such as disclosed in U.S. Pat. No. 5,190,931.

DETAILED DESCRIPTION OF THE INVENTION

As indicated the present invention relates in its first aspect to fungi, wherein the areA gene by recombinant DNA technology has been modified such that it cannot be expressed in a way providing for a functional AreA activator.

This object may specifically be obtained by deletion or disruption of the areA gene.

The cloning of the areA gene is described in the Examples.

AreA homologs from other fungi could be cloned either by cross hybridization with one of the already known genes or by complementation of areA mutants; e.g. *A. nidulans* areA-18 or the *A. oryzae* areA deleted strain described in this application.

Methods for deleting or disrupting a gene are specifically described in WO 90/00192 (Genencor).

Methods for substituting DNA in a gene are also generally known, and can be accomplished by substituting one or more continuous parts of the gene, but it may also be obtained by site directed mutagenesis generating a DNA sequence encoding a AreA activator variant that is not functional.

Another method by which such an object may be obtained is by using anti-sense technology.

The anti-sense technology and how to employ it is described in detail in the aforementioned U.S. Patent No. 5,190,931 (University of New York).

A further method of obtaining said inactivation is by inserting extra DNA internally in the areA gene, thereby giving rise to the expression of a dysfunctional activator protein.

In connection with this method information provided by the cloning can be used to make DNA constructs that can be integrated into the areA gene, and even replace it with another gene, such as the pyrG gene.

A further method of avoiding the presence of the area activator is by interfering with the regulation of the expression signals regulating the expression of the areA gene itself.

According to the invention the fungus preferably belongs to a genus selected from the group comprising Aspergillus, Trichoderma, Humicola, Candida, Acremonium, Fusarium, and Penicillium Among these genera species selected from the group comprising *A. oryzae, A. niger, A. awamori, A. phoenicis, A. japonicus, A. foetidus, A. nidulans, T. reesei, T. harzianum, H. insulens, H. lanuginosa, F. graminearum, F. solani, P. chrysogenum*, and others are preferred.

As indicated the invention also is meant to encompass the method for producing the fungi of the first aspect of the invention, and wherein said inactivation has been obtained by deletion of the areA gene, which method comprises
i) cloning of homologues of the area gene from a fungus of interest,
ii) producing a DNA construct comprising the areA gene wherein an internal part has been substituted, deleted, or extra DNA has been inserted,
iii) transforming said fungus with the construct, and
iv) selecting transformants which are areA.

Also included is the method for producing the fungi, wherein the inactivation has been obtained by using anti-sense technology. Such a method comprising
i) construction of an expression plasmid which gives rise to synthesis of a RNA molecule complementary to the mRNA transcribed from the areA gene,
ii) transformation of the host fungus with said expression plasmid and a suitable marker, either on separate plasmids or on the same plasmid,
iii) selection of transformants using said marker, and
iv) screening transformants for strains exhibiting a reduction in the synthesis of the AreA product, e.g. by analysis of the growth on various nitrogen sources.

A further aspect of the invention is meant to comprise DNA constructs for use in the above mentioned methods.

In respect of the former method said DNA constructs may comprise the areA gene wherein an internal part has been substituted, deleted, or extra DNA has been inserted.

The DNA construct may furthermore also comprise DNA sequences encoding a protein product of interest, such as those mentioned later.

In respect of the latter anti-sense method the DNA construct may comprise an inverted DNA sequence of the areA gene connected to a functional promoter, whereby the mRNA is at least partially complementary to mRNA produced from the area gene.

A further aspect of the invention relates to a process for the production of a desired gene product, preferably a secreted gene product, whereby a fungus according to the invention is cultivated in a suitable growth medium at appropriate conditions and the desired gene product is recovered and purified.

In the case of a gene product expressed by a heterologous gene the DNA sequence coding for the desired gene product may be a part of the DNA construct used for producing said fungus.

Normally, however, a separate transformation of the fungus of the invention is performed in order to make the fungus capable of producing the desired product.

Methods for transforming fungi are well known in the art, cf. e.g. EP 0 184 438 A2 (Gist-Brocades N.V.) and EP application no. 87103806 (Novo Nordisk A/S) and.

For indigenous products this is of course not necessary, but in order to increase the production it may be an advantage to provide for multiple copies of the gene encoding the protein of interest to be incorporated into the host.

The desired gene product is generally a peptide or protein, preferably an enzyme.

Among enzymes it is preferably selected from the group comprising proteases, such as trypsin and chymosin; lipases, cutinases, cellulases, xylanases, laccases, pectinases, etc.

Another type of desired gene product is generally a therapeutically active peptide or protein.

Among the therapeutically active peptide or protein the protein preferably is selected from the group comprising insulin, growth hormone, glucagon, somatostatin, interferons, PDGF, factor VII, factor VIII, urokinase, t-PA, CSF, lactoferrin, TPO etc.

The invention is explained in further detail in the Examples given below. These should, however, not in any way be construed as limiting the scope of the invention as defined in the appended claims.

EXAMPLES

Materials and Methods

Strains

*A. oryzae*, IFO4177: available from Institute for Fermentation, Osaka; 17–25 Juso Hammachi 2-Chome Yodogawa-Ku, Osaka, Japan.

ToC913: The construction of this strain is described in the Examples.

Genes areA: This gene codes for a regulatory protein controlling nitrogen catabolism.

pyrG: This gene codes for orotidine-S'-phosphate decarboxylase, an enzyme involved in the biosynthesis of uridine.

bar: This gene was originally isolated from Streptomyces hygroscopicus and codes for phosphinothricin acetyltransferase. The enzyme modifies phosphinothricin (=glufosinate) and thereby inactivates this compound which is toxic to bacteria, fungi and plants.

Plasmids

PUC118: Viera and Mesing *J. Meth. Enzymol.* 1987 153 3–11 pS02: The construction of this plasmid is described in the Examples.

pJers4: A 2.0 kb subclone of pS02 in pUC118. pJers4 contains a functional *A. oryzae* pyrG gene.

pS05: The construction of this plasmid from pS02 is described in the Examples.

pToC56: The construction of this plasmid is described in EP application no. 87103806.

pToC266: The construction of this plasmid is described in the Examples.

pMT1606: The construction of this plasmid from pBP1T (B. Straubinger et al. Fungal Genetics Newsletter 39(1992) :82–83) and p775 (EP application no. 87103806) is described in the Examples.

p777: The construction of this plasmid is described in EP application no. 87103806.

pHW470: The construction of this plasmid is described in the Examples.

EXAMPLE 1

Construction of an *Aspergillus oryzae* areAΔ strain.

The areAΔ strain was constructed by the following steps. The *A. oryzae* pyrG gene was cloned and an *A. oryzae* pyrG mutant strain was isolated. The areA gene from *A. oryzae* was cloned. The pyrG mutant was transformed with a plasmid carrying the pyrG gene inserted between DNA fragments upstream and downstream from the areA gene. The coding region for areA was not present on the plasmid. Transformants were selected for their ability to grow in the absence of uridine and in the presence of chlorate. This double selection selects both for a functional pyrG gene and for areA minus. Strains obtained by this selection procedure were finally screened by Southern analysis to identify those in which the chromosomal areA gene was substituted by the pyrG gene.

Cloning of the *A. oryzae* pyrG gene.

The *A. oryzae* pyrG gene was cloned by cross hybridization with the *A. niger* pyrG gene (W. van Hartingsveldt et al., *Mol. Gen. Genet* 206:71–75 (1987)). A lambda library of partial SauIIIA digested *A. oryzae* IFO4177 DNA was probed at low stringency with a 1 kb DNA fragment from the *A. niger* pyrG gene. A 3.8 kb HindIII fragment from a positive clone was subcloned into a pUC118 vector. The resultant plasmid, pS02, was shown to contain the pyrG gene by complementation of an *A. niger* pyrG mutant.

Construction of an *A. oryzae* pyrG minus strain.

A pyrG deletion plasmid, pS05, containing about 1 kb of pyrG flanking sequences on each end was constructed from the plasmid pS02. *A. oryzae* IFO4177 was transformed with this construct and transformants were selected by resistance to 5-fluoro-orotic acid, a phenotype characteristic of pyrG mutants. One transformant, HowB101, was shown by Southern analysis to have the expected deletion at the pyrG locus. Being a pyrG mutant HowB101 requires uridine for growth. HowB101 can be transformed with the wt pyrG gene by selection for ability to grow without uridine.

The steps involved in the construction of HowB101 are illustrated in FIG. 1.

Cloning of the areA gene.

Figure 2:
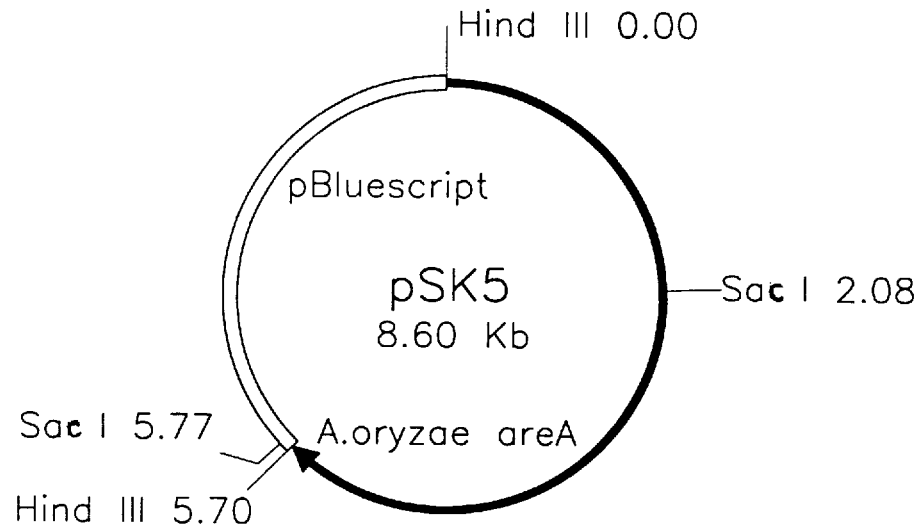
FIG. 2 shows the steps involved in the construction of pSK5 and pSK9.
Figure 2:
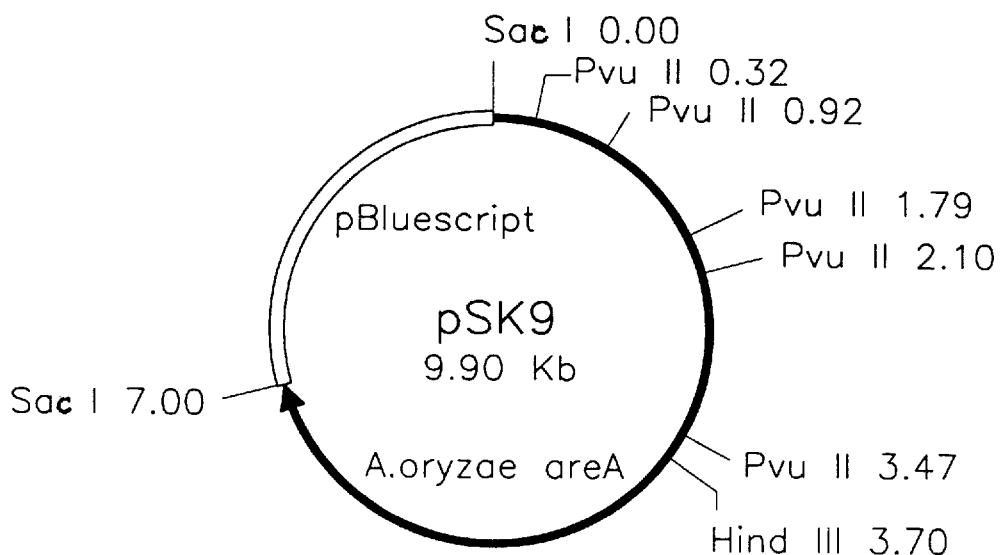

The *A. oryzae* areA gene was cloned by cross hybridization to the *A. nidulans* areA gene (B. Kudla et al., *EMBO J.* 9:1355–1364 (1990)). A genomic library of *A. oryzae* IFO4177 was prepared by partial digestion of chromosomal DNA with SauIIIA and cloning of the obtained DNA fragments into the vector λGEM-II (obtained from Promega). Cross hybridization of the library with the *A. nidulans* areA gene was performed in 40% formamide at 37° C. Hybridizing λ clones were isolated and from these fragments were sub-cloned into the vector pBluescript SK+ (obtained from Stratagene) giving rise to the plasmids pSK5 and pSK9 illustrated in FIG. 2. The cloned gene was able to complement an *A. nidulans* areA mutant, proving that it is indeed the *A. oryzae* areA homolog. 5643bp of the clone was sequenced, and comparison of the sequences of the *A. oryzae* and the *A. nidulans* areA genes shows that they are highly homologous. The sequence of the *A. oryzae* areA gene is shown in SEQ ID No. 1.

Construction of the areA deletion plasmid.

Figure 3A:
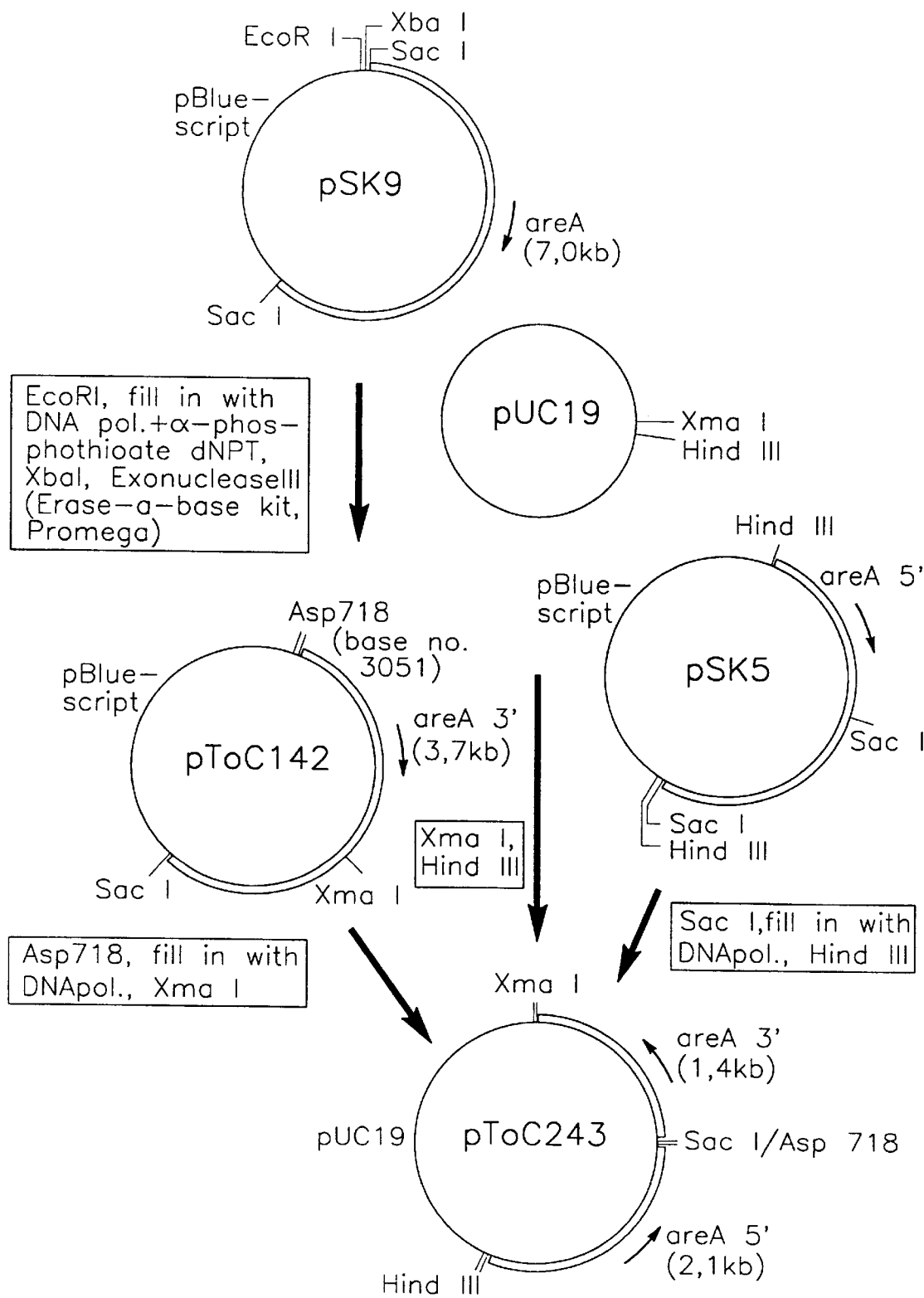
FIGS. 3a and 3b show the steps involved in the construction of pToC266.
Figure 3B:
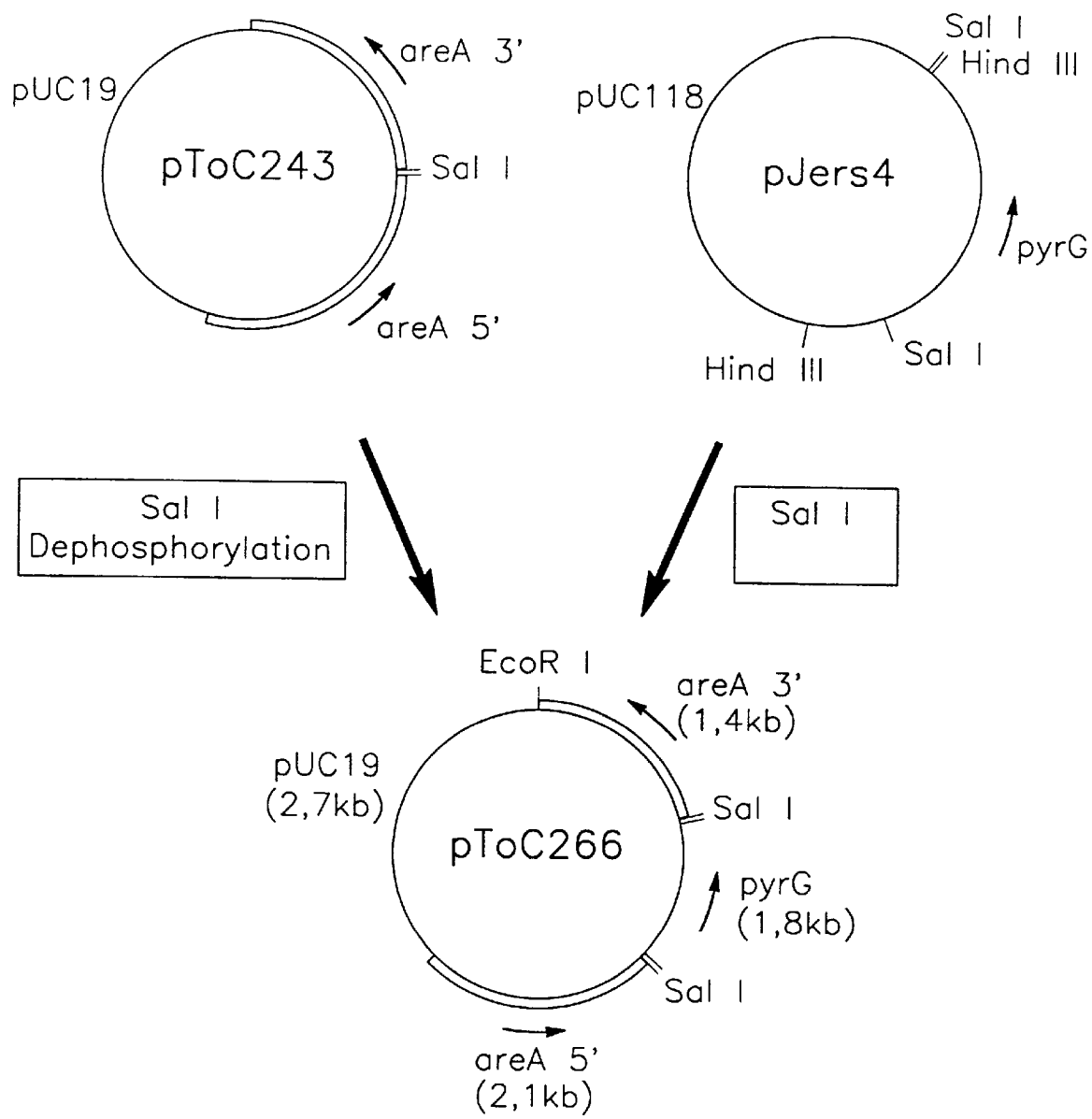

In order to delete the areA gene from the *A. oryzae* chromosome the plasmid pToC266 was constructed. pToC266 contains a 2.1 kb DNA fragment originating upstream of the areA gene (isolated from pSK5) and a 1.4 kb DNA fragment originating downstream from the areA gene (isolated from pSK9). The two fragments are separated by appr. 3.2 kb in the genome, the coding region is situated in this part of the gene. The *A. oryzae* pyrG gene from pJers4 was inserted between the areA upstream and downstream DNA fragments. The construction of pToC266 is illustrated in FIGS. 3*a* and 3*b*. pToC266 has a unique EcoRI site and was linearized nearized by cutting with this restriction enzyme before used in transformations.

Selection of *A. oryzae* areAΔ strains.

*A. oryzae* HowB101 was transformed with linearized pToC266. Transformants were selected on minimal plates (Cove *Biochem. biophy. Acta* (1966) 113 51–56) containing 5% sodium chlorate and 0.5 mM ammonium sulfate and 1% glucose. Transformants were thus subject to a double selection, both for having obtained the pyrG gene by being able to grow without addition of uridine and for chlorate resistance. Chlorate resistance is one of the phenotypes of *A. nidulans* areA mutants (H. N. Arst and D. J. Cove, *MGG* 126:111–141 (1973)). Weakly growing transformants were reisolated twice on the same type of plates. Three independent transformants named ToC913, ToC919 and ToC920 were subjected to growth test on different nitrogen sources. They grew well on glutamine, but weakly on other nitrogen sources tested, including ammonia. Southern analysis showed that the three strains have the lost the areA structural gene, which had been replaced by the pyrG gene.

areAA strains can also be obtained by selection of transformants of linearized pToC266 on minimal plates containing glutamine as nitrogen source. In one such experiment one out of 25 transformants was an areAΔ strain.

EXAMPLE 2

Construction of pMT1606

A plasmid containing the bar gene from Streptomyces hygroscopius (C. J. Thompson et. al, *EMBO J.* 6 : 2519–2523 (1987)) inserted after the *A. oryzae* TAKA-amylase promoter and followed by a fragment containing the transcriptional terminator and polyadenylation signal from the *A. niger* gla gene was constructed.

Figure 4:
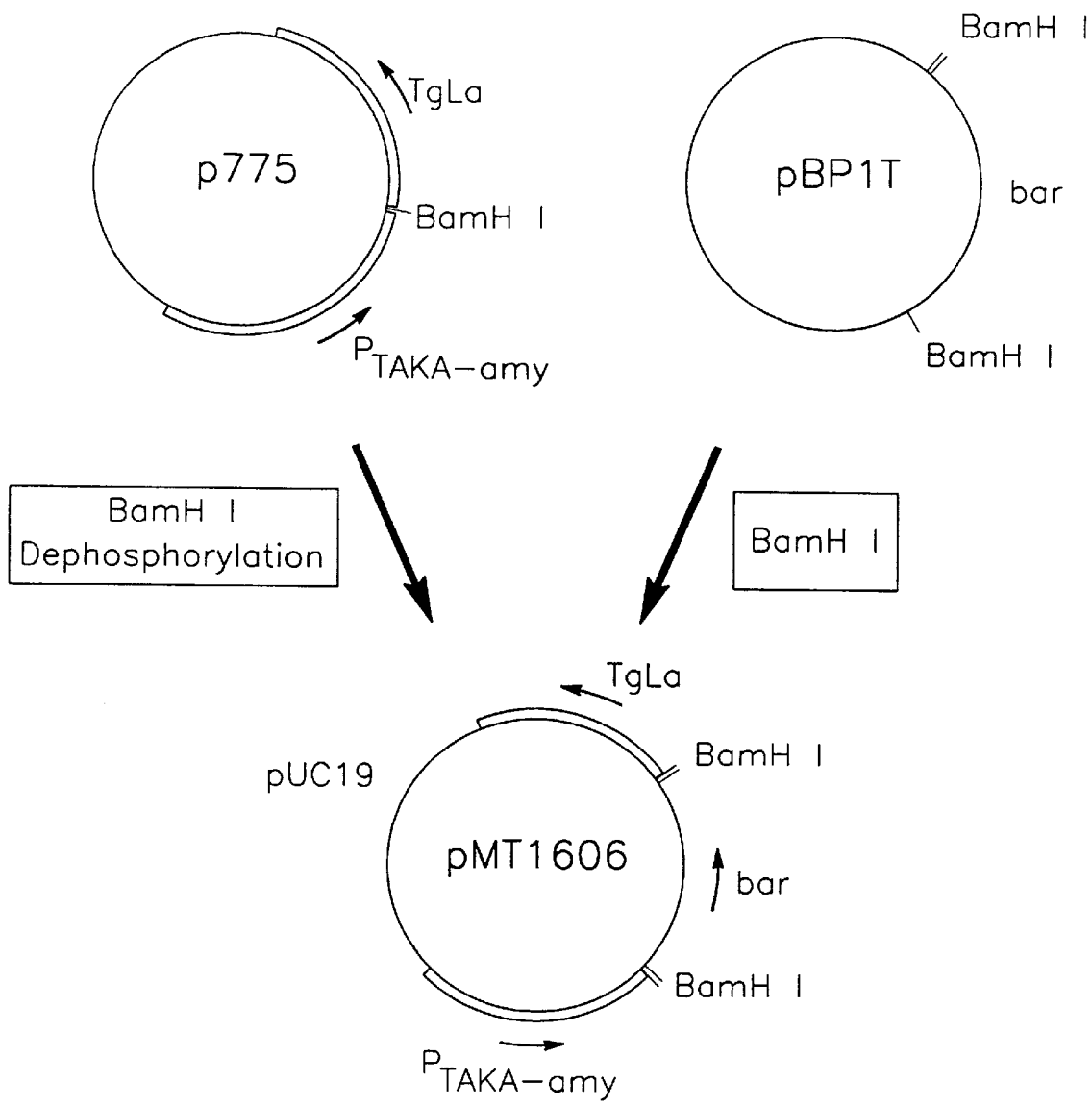
FIG. 4 shows the steps involved in the construction of pMT1606.

The plasmid, pMT1606, can be used for selection of glufosinate resistant transformants of *A. oryzae*. pMT1606 was constructed by isolating the bar gene from the plasmid pBP1T (B. Straubinger et. al, Fungal Genetics Newsletter 39:82–83 (1992)) and cloning it into the fungal expression plasmid p775 described in EP application no. 87103806. FIG. 4 illustrates the construction of pMT1606.

EXAMPLE 3

Production of chymosin in ToC913 (*A. oryzae* IFO4177 areAΔ)

Figure 5:
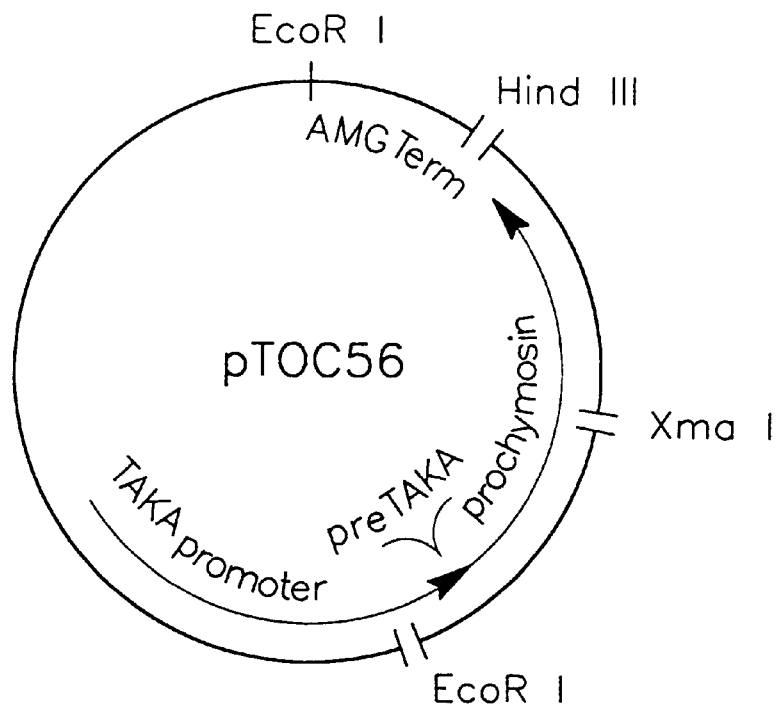
FIG. 5 shows the steps involved in the construction of pToC56.

The *A. oryzae* areAΔ strain ToC913 was transformed with the plasmid pToC56 (FIG. 5), which is a fungal expression plasmid for the mammalian enzyme chymosin, by co-transformation with pMT1606. Construction of the plasmid pToC56 is described in EP application no. 87103806.

Transformants were selected for growth on minimal medium containing 10 mM ammonium and 1 mg/ml glufosinate and screened for the presence of pToC56 by the ability to produce chymosin. Three transformants were grown in shake flasks in minimal medium containing maltodextrin and glutamine for 4 days at 30° C.

Two transformants of pToC56 in IFO4177 (obtained as described in EP 87103806) as well as untransformed IFO4177 and ToC913 were grown along with the ToC913 transformants.

Samples of the fermentation broth were taken every day and applied to SDS-Page and Western blotting. The blotting membrane was incubated with chymosin specific rabbit antibody followed by goat rabbit antibody coupled to peroxidase. Staining of the membrane showed that the supernatants from transformants of IFO4177 contained small amounts of chymosin or degradation products thereof on the first and second day of fermentation and nothing later in fermentation.

Transformants of ToC913 contained at least ten times more full size chymosin. The amount of chymosin in the supernatants increased for the first two-three days and then remained constant.

Supernatants from the third and fourth day of fermentation of IFO4177, ToC913, a transformant of pToC56 in ToC913, and a transformant in IFO4177 were applied to an isoelectric focussing gel and electrophoresis was performed. The pH gradient was from 3.5 to 9.5. After electrophoresis the gel was rinsed with a buffer at pH =7.0 containing 2 mM $Zn^{2+}$ and overlayed with an agar containing 0.5% casein. The gel was incubated at 45° C. untill protease activity was visible.

In samples from IFO4177 three bands with protease activity could be seen; one with an alkaline pI and two with acidic pI's.

In samples from the pToC56 transformant of IFO4177 a faint reaction from chymosin could be seen, which partially overlapped with one of the acidic bands found in untransformed IFO4177, the protease with most acidic pI was barely visible, while the protease with the alkaline pI was clearly visible along with one or more band with an almost neutral pI.

In the samples from ToC913 no protease activity was detected, while the sample from the pToCS6 transformant of ToC913 showed a strong chymosin signal. No other proteases were detected in samples from this transformant.

EXAMPLE 4

Production of human trypsin I in ToC913 (*A. oxyzae* IFO4177 areAΔ)

A cDNA encoding human pancreatic trypsinogen I (TRYI) was isolated using standard procedures and the sequence published by M. Emi et al, *Gene* (1986) 41:305–310(cf. Danish patent application no. 693/95). A BamH1 site (GGATCC) was introduced immediately upstream of the start codon (ATG(Met)) with the short sequence ACC between.

This BamH1 site was used to fuse the cDNA to the BamH1 linker in the Taka-amylase promoter in the fungal expression plasmid p777 described in EP application no. 87103806. The 3' end of the cDNA was fused 41 bp downstream of the stop codon to a Nru1 site in p777. This inserts the TRYI cDNA between the *A. oryzae* Taka-amylase promoter and the *A. niger* glucoamylase transcription terminator. The resulting plasmid was called pHW470 (cf. Danish patent application no. 693/95).

pHW470 was transformed into ToC913 by co-transformation with the plasmid pMT1606. BASTA resistant transformants were reisolated twice through conidiospores. 8 transformants were grown for four days at 30° C. in YPM (YPD(Sherman, F. et al (1981) *Methods in Yeast Genetics*. Cold Spring Harbor Laboratory. Cold Spring Harbor, N.Y.)) in which the glucose was replaced with 2% maltose). Supernatants were analysed for the content of human trypsin by SDS-PAGE followed by Western blotting and incubation with a rabbit antibody raised against porcine trypsin. The blotting membrane was then incubated with goat anti rabbit antibody coupled to peroxidase and reacted with 3-amino-9-ethyl carbazole. Supernatants from three of the transformants contained a stained band of the expected size. The concentration of trypsin in the three positive supernatants was 2–5 mg/l.

The presence of trypsin was further verified by incubation of samples of supernatants with L-Benzoyl-arginoyl-paranitro anilide (L-BAPNA). Samples from the three immuno positive strains cleaved the substrate, which resulted in the development of a yellow colour. Samples from ToC913 and IFO4177 did not show any activity against this substrate. The specific activity of human trypsin in this assay in not known, it is thus not possible to calculate the concentration of trypsin in the supernatants from these data.

Transformants of pHW470 in the wild type strain IFO4177 were also made. More than 20 L-BAPNA positive transformants were looked at, but it was not possible to detect any immonoreactive bands in supernatants from these transformants. The detection limit was approximately 0.5 mg/l in this assay.

---

We claim:

1. An *Aspergillus oryzae* cell comprising a modified areA gene, wherein said modification reduces the synthesis of a functional areA gene product and wherein the modification of the areA gene is (a) a deletion of all or parts of SEQ ID NO:1; or (b) insertion of extra DNA internally into SEQ ID NO:1.

2. A method for producing the *Aspergillus oryzae* cell of claim 1, wherein said method comprises:

(a) cloning the area gene comprising SEQ ID NO:1 from *Aspergillus oryzae;*

(b) producing a DNA construct comprising the area gene wherein an internal part of SEQ ID NO:1 has been substituted or deleted, or extra DNA has been inserted into SEQ ID NO:1;

(c) transforming said *Aspergillus oryzae* with the construct; and (d) selecting transformants which exhibit a reduced synthesis of a functional area gene product.

3. A process for producing a polypeptide comprising the steps of:

(a) cultivating the *Aspergillus oryzae* cell of claim 1; and (b) recovering and purifying the polypeptide.

4. The process of claim 3, wherein the *Aspergillus oryzae* cell has been transformed with a DNA sequence coding for the polypeptide.

5. The process of claim 3, wherein the polypeptide is a fungal polypeptide.

6. The process of claim 3, wherein the polypeptide is a secreted protein.

7. The process of claim 6, wherein the polypeptide is secreted to the extracellular medium.

8. An isolated DNA sequence coding for the areA gene from *Aspergillus oryzae* comprising SEQ ID NO:1.

* * * * *